United States Patent [19]
Di Bella

[11] 4,031,144
[45] June 21, 1977

[54] CHLORINATION OF TOLUENE

[75] Inventor: Eugene P. Di Bella, Piscataway, N.J.

[73] Assignee: Tenneco Chemicals, Inc., Saddle Brook, N.J.

[22] Filed: Mar. 22, 1976

[21] Appl. No.: 669,438

[52] U.S. Cl. ............................................. 260/650 R
[51] Int. Cl.² ........................................ C07C 25/28
[58] Field of Search ................................ 260/650 R

[56] References Cited
UNITED STATES PATENTS
3,226,447  12/1965  Bing et al. .................. 260/650 R

*Primary Examiner*—C. Davis
*Attorney, Agent, or Firm*—Evelyn Berlow

[57] ABSTRACT

Monochlorotoluene that contains at least 45 percent of para-chlorotoluene is prepared by contacting toluene with chlorine in the presence of a catalyst system that contains a ferrocene compound and a sulfur compound.

9 Claims, No Drawings

CHLORINATION OF TOLUENE

This invention relates to a process for the production of chlorotoluenes. More particularly, it relates to a process for the production of monochlorinated toluene whereby there is obtained a mixture of monochlorotoluene isomers of unusually high parachlorotoluene content. It further relates to a process for the production of mixtures of polychlorotoluenes that contain unusually large amounts of isomers that have a chlorine atom in the 4-position of the aromatic ring.

In accordance with this invention, it has been found that when toluene is chlorinated in the presence of a catalyst system that contains a ferrocene compound and a sulfur compound the monochlorotoluene mixture that is formed has a para-isomer content that is significantly higher than that obtained using any of the previously-known iron-sulfur catalyst systems.

The catalyst systems of this invention, which are completely soluble in toluene and monochlorotoluene, are of particular value in the continuous production of monochlorotoluene by procedures that require residence times in the reaction zone of 1 minute or less. Under such conditions, the rate of solubilization of materials such as ferrous sulfide or free iron is too slow to permit efficient ring chlorination of the toluene. In addition, the novel catalyst system may be introduced as a toluene solution into the reaction zone of the chlorination apparatus, whereas other catalyst systems that contain iron or iron compounds require the undesirable separate and continuous addition of solid materials to the reaction zone.

The catalyst systems of this invention comprise a ferrocene compound and a co-catalyst that is sulfur or a compound that contains at least one divalent sulfur atom. The catalyst system must contain at least 0.1 part by weight of the co-catalyst per part by weight of the ferrocene compound if the desired high proportion of para-chlorotoluene is to be obtained. In most cases, 0.4 to 0.6 part by weight of the sulfur compound is used per part by weight of the ferrocene compound. The use of a larger amount of the sulfur co-catalyst does not result in a further increase in the para-isomer content of the product.

The ferrocene component of the catalyst system is a dicyclopentadienyl iron compound that is prepared by the reaction of a ferrous compound, such as ferrous chloride or ferrous sulfate, with an alkali metal salt of cyclopentadiene or an alkyl-substituted cyclopentadiene. The preferred catalyst and the one most commonly used in the process of this invention is dicyclopentadienyl iron (ferrocene). Other useful ferrocene catalysts are derived from cyclopentadienes that have as substituents 1 or 2 lower alkyl groups. Illustrative of these alkyl-substituted ferrocenes are the following: (methylcyclopentadienyl)(cyclopentadienyl) iron, (butylcyclopentadienyl)(cyclopentadienyl) iron, (hexylcyclopentadienyl) (cyclopentadienyl) iron, (dimethylcyclopentadienyl)(methylcyclopentadienyl) iron, (dibutylcyclopentadienyl)(ethylcyclopentadienyl) iron, bis(ethylcyclopentadienyl) iron, bis (hexylcyclopentadienyl) iron, bis(dimethylcyclopentadienyl) iron, bis(butylcyclopentadienyl) iron, and the like. The catalyst system may contain one or more of the ferrocene compounds.

The sulfur compounds that may be used as co-catalysts in the catalyst systems include sulfur and a wide variety of organic and inorganic compounds that contain one or more divalent sulfur atoms and that are soluble to at least a limited extent in the reaction mixture. These include sulfur, sulfur monochloride, sulfur dichloride, carbon disulfide, thiophenes, thiophanes, alkyl-, cycloalkyl-, aryl-, and aralkyl mercaptans and dimercaptans, thioethers, and the like. The preferred co-catalysts are sulfur monochloride, sulfur, and sulfur-containing compounds that are converted to sulfur monochloride under the conditions of ring chlorination such a sulfur dichloride and carbon disulfide.

The amount of the catalyst system that is used is that which will provide at least 0.1 gram of the ferrocene compound per mole of toluene. An amount that will provide from 0.5 to 1.5 grams of the ferrocene compound per mole of toluene is preferred because it makes possible a reaction rate that is fast enough for commercial operation of the process while it totally suppresses competitive side-chain chlorination and ring-addition reactions.

The chlorination of toluene may be carried out by procedures that are well known in the art. For example, chlorine may be added to a reaction mixture containing toluene and catalyst and the addition of chlorine continued until the increase in the weight of the reaction mixture indicates that the desired amount of chlorine has reacted with the toluene. In the production of monochlorotoluene, the reaction is usually continued until from 0.7 to 1.1 gram atoms of chlorine, and preferably approximately 1 gram atom of chlorine has reacted per mole of toluene. Polychlorotoluens result when from 2 to 5 gram atoms of chlorine is reacted per mole of toluene.

The chlorination reaction may be carried out at temperatures in the range of $-20°$ to $70°$ C., with $20°$ to $50°$ C. the preferred temperature range. At temperatures below $-20°$ C., the reaction takes place too slowly to be of commercial interest. At temperatures above $70°$ C., there is a tendency for side-chain chlorinated reaction by-products to form. Since chlorination is an exothermic reaction, external cooling may be required to maintain the reaction temperature in the desired range.

The rate at which chlorine is added to the reaction mixture does not have an appreciable effect on the yield of chlorotoluene or on the isomer distribution of the product.

When toluene is monochlorinated in accordance with the present invention, the reaction product contains at least 75 percent and in most cases at least 85 percent of monochlorotoluene and small amounts of toluene and dichlorotoluene. The monochlorotoluene fraction, which may be separated from the toluene and dichlorotoluene by fractional distillation or other known technique, contains at least 45 percent and in most cases at least 48 percent of para-chlorotoluene, the remainder being orthochlorotoluene and very small amounts of meta-chlorotoluene. The para-chlorotoluene may be separated from its isomers by fractional distillation.

When the chlorination of toluene in accordance with this invention is carried beyond the monochlorotoluene stage, polychlorotoluene mixtures are obtained that consist principally of compounds that have a chlorine atom in the 4-position of the aromatic ring, with the amount of such isomers directly dependent upon the para-chlorotoluene content of the monochlorotoluene mixture. To obtain a maximum yield of these polychlorotoluene isomers, the monochlorotoluene mixture may be fractionally distilled to yield a fraction containing a major amount of parachlorotoluene, which may then be further chlorinated in the presence of the ring chlorination catalyst of this invention.

The invention is illustrated by the following example.

EXAMPLE

A mixture of 184 grams (2.0 moles) of toluene, 2 grams of ferrocene, and 1 grams of sulfur monochloride in a glass chlorination vessel was chlorinated by passing a stream of gaseous chlorine over its surface at the rate of 60 grams per hour until a weight increase of 71 grams (1 gram atom of chlorine per mole of toluene) had been attained. During the chlorination, the reaction mixture was stirred, and its temperature was maintained at 34°–36° C. by means of external cooling. Samples were withdrawn periodically during the chlorination and analyzed by gas-liquid chromatography. The results obtained are summarized in the following table.

COMPARATIVE EXAMPLES

For comparative purposes, a number of ring-chlorination catalysts containing iron or iron and sulfur were used in the chlorination reaction described in the foregoing example. The catalysts used and the results obtained are summarized in the Table.

Each of the other ferrocene compounds and sulfur compounds disclosed hereinbefore can be used in a similar way in the production of monochlorotoluene that has an unusually high para-chlorotoluene content.

stituted ferrocenes derived from cyclopentadienes having as substituent one or two lower alkyl groups, and mixtures thereof and a co-catalyst selected from the group consisting of sulfur, sulfur monochloride, sulfur dichloride, carbon disulfide, and mixtures thereof in the amount of at least 0.1 part by weight of said co-catalyst per part by weight of the ferrocene compound.

2. The process of claim 1 wherein the catalyst system contains 0.4 to 0.6 part by weight of said co-catalyst per part by weight of the ferrocene compound.

3. The process of claim 1 wherein the ferrocene compound is ferrocene.

4. The process of claim 1 wherein the co-catalyst is sulfur monochloride.

5. The process of claim 1 wherein the amount of the catalyst system that is used is that which will provide at least 0.1 gram of the ferrocene compound per mole of toluene.

6. The process of claim 1 wherein the amount of the catalyst system that is used is that which will provide from 0.5 to 1.5 grams of the ferrocene compound per mole of toluene.

7. The process of claim 1 wherein approximately 1 gram atom of chlorine is reacted per mole of toluene.

8. The process of claim 1 wherein the chlorination is carried out at a temperature in the range of 20° to 50° C.

9. The process of claim 1 wherein toluene is contacted with chlorine until from 0.7 gram atom to 1.1 gram atoms of chlorine has reacted per mole of toluene at a temperature in the range of 20° to 50° C. and in the presence of a catalyst system that comprises ferrocene

TABLE

| Catalyst Composition | Amount of Catalyst (g. per mole of toluene) | Chlorination Level (gram atoms Cl/mole of toluene) | Product Composition (% by Wt.)* | | | | Isomer Distribution in Monochlorotoluene (%) | | |
|---|---|---|---|---|---|---|---|---|---|
| | | | Toluene | Mono-chloro-toluene | Di-chloro-toluene | Tri-chloro-toluene | ortho | meta | para |
| Example Ferrocene Sulfur Mono- chloride | 1.0 ⎫ 0.5 ⎭ | 0.70 0.85 0.95 1.00 | 24.1 11.7 3.8 0 | 75.7 88.0 95.6 97.3 | 0.2 0.3 0.6 2.7 | 0 0 0 0 | 51.2 50.7 50.6 50.4 | 0.32 0.26 0.26 0 | 48.5 49.0 49.2 49.6 |
| Comparative Examples | | | | | | | | | |
| Ferric Chloride Sulfur Mono- chloride | 1.0 ⎫ 0.5 ⎭ | 0.78 0.87 0.99 | 17.3 10.2 0.9 | 81.4 88.1 96.3 | 1.1 1.4 2.4 | 0.2 0.3 0.4 | 55.5 55.3 58.2 | 0.51 0.53 0.37 | 44.0 44.2 44.4 |
| Iron Sulfur Mono- chloride | 0.5 ⎫ 0.5 ⎭ | 0.81 0.96 1.00 | 14.7 3.5 0.6 | 85.0 95.9 98.2 | 0.3 0.7 1.2 | 0 0 0 | 54.1 54.0 53.9 | 0.52 0.45 0.38 | 45.3 45.5 45.7 |
| Ferrous Sulfide | 1.0 | 0.90 0.95 0.98 | 7.1 4.1 1.8 | 92.1 95.1 97.1 | 0.8 0.8 1.1 | 0 0 0 | 52.9 52.8 52.8 | 0.43 0.44 0.33 | 46.7 46.8 46.8 |
| Ferric Sulfide Ferrocene Iron | 1.0 1.0 0.5 | 0.98 0.96 0.97 | 1.5 2.7 2.0 | 97.5 94.8 97.1 | 1.0 2.5 1.0 | 0 0 0 | 57.0 61.5 61.2 | 0.62 0.80 0.60 | 42.4 37.7 38.2 |

*The gas-liquid chromatography data have been normalized to exclude the <0.5% of volatile material present in some catalyst components. No benzyl chloride was detected in any instance.

What is claimed is:

1. The process for the production of monochlorotoluene containing at least 45 percent of parachlorotoluene which comprises contacting toluene with chlorine until from 0.7 to 1.1 gram atoms of chlorine has reacted per mole of toluene at a temperature in the range of −20° to 70° C. and in the presence of a catalyst system that comprises a ferrocene compound selected from the group consisting of ferrocene, alkyl-suband sulfur monochloride in the amounts of 0.4 to 0.6 part by weight of sulfur monochloride per part by weight of ferrocene and from 0.5 to 1.5 grams of ferrocene per mole of toluene, thereby forming a mixture of chlorotoluenes that contains at least 45 percent of para-chlorotoluene, and separating para-chlorotoluene from said mixture of chlorotoluenes by fractional distillation.

* * * * *